United States Patent [19]

Lauer et al.

[11] Patent Number: 5,399,158
[45] Date of Patent: Mar. 21, 1995

[54] METHOD OF LYSING THROMBI

[75] Inventors: Carl G. Lauer, El Paso, Tex.; Barbara Alving, Bethesda, Md.

[73] Assignee: The United States of America as represented by the Secretary of the Army, Washington, D.C.

[21] Appl. No.: 9,599

[22] Filed: Jan. 27, 1993

Related U.S. Application Data

[63] Continuation-in-part of Ser. No. 531,281, May 31, 1990, abandoned.

[51] Int. Cl.⁶ .............................................. A61B 17/20
[52] U.S. Cl. ............................................ 604/22; 601/2
[58] Field of Search .................... 604/22, 49, 52, 53; 128/24 AA, 898; 606/169–171; 601/2

[56] References Cited

U.S. PATENT DOCUMENTS

| | | | |
|---|---|---|---|
| 3,352,303 | 11/1967 | Delaney | 604/22 |
| 3,710,779 | 1/1973 | Bonnell et al. | 128/24 AA |
| 3,735,755 | 5/1973 | Eggleton et al. | 128/24 AA |
| 4,002,221 | 1/1977 | Buchalter | 128/24 AA |
| 4,692,139 | 9/1987 | Stiles | 604/22 |
| 4,721,106 | 1/1988 | Kurtze et al. | 604/22 |
| 4,825,851 | 5/1989 | Cocks et al. | 604/22 |
| 4,870,953 | 10/1989 | DonMichael et al. | 604/22 |
| 4,889,122 | 12/1989 | Watmough et al. | 128/24 AA |
| 4,905,672 | 3/1990 | Schwarze et al. | 128/24 AA |
| 5,018,508 | 5/1991 | Fry et al. | 128/24 AA |
| 5,050,588 | 9/1991 | Grey et al. | 128/24 AA |
| 5,058,590 | 10/1991 | Wurster | 604/22 |
| 5,143,073 | 9/1992 | Dory | 128/24 AA |
| 5,158,071 | 10/1992 | Umemura et al. | 128/24 AA |
| 5,247,935 | 9/1993 | Cline et al. | 128/24 AA |

Primary Examiner—C. Fred Rosenbaum
Assistant Examiner—Michael Rafa
Attorney, Agent, or Firm—Werten F. W. Bellamy; John Francis Moran

[57] ABSTRACT

This invention relates to the prevention and treatment of thrombi using plasminogen activators, including t-PA, urokinases, and streptokinases, in conjunction with intermittent (pulsed mode) ultrasound. A preferred modality interposes liquid-containing interface between the skin of the patient and the transducer of the ultrasound generator.

20 Claims, 1 Drawing Sheet

METHOD OF LYSING THROMBI

This application is a continuation-in-part of U.S. patent application Ser. No. 07/531,281, filed May 31, 1990, ABN.

FIELD OF THE INVENTION

This invention relates to the prevention and treatment of thrombi using plasminogen activators in conjunction with intermittent (pulsed mode) ultrasound. A preferred modality interposes liquid-containing interface between the skin of the patient and the transducer of the ultrasound generator.

BACKGROUND OF THE INVENTION

Plasminogen activating agents including streptokinase, urokinase, tissue plasminogen activator (t-PA), and their analogues have been administered as lytic agents for treatment of arterial and venous thrombosis. Although such agents as t-PA are efficacious for lysis of coronary thrombi and pulmonary emboli, relatively high concentrations are required. (Marder V. J., Sherry S.; "Thrombolytic Therapy: Current Status" *N Engl J Med* 318:1512-20 (1988). Marder V. J., Sherry S.; "Thrombolytic Therapy: Current Status", *N Engl J Med* 318:1585-95 (1988). Vaughan D. E., Goldhaber S. Z., Kim J., Loscalzo J.; "Recombinant Tissue Plasminogen Activator in Patients Pulmonary Embolism . . . " *Circulation* 75:1200-03 (1987).) The need for high concentrations may be due, in part, to the paucity of fibrin binding sites for t-PA on the surface of whole blood clots. In the absence of binding to fibrin, t-PA has greatly reduced efficacy in activating plasminogen and inducing clot lysis. In clinical practice, t-PA can be directly injected into the site of thrombus with percutaneous transluminal catheters rather than infused systemically. Presumably this approach improves lysis by increasing the surface area of fibrin available for t-PA binding.

Ultrasound has been used without exogenous t-PA to disrupt peripheral arterial and venous thrombi in animal models and to open atherosclerotic occlusions of peripheral arteries in selected patients. To achieve these effects, ultrasound was used at a frequency (20 kHz) and intensity that caused cavitation, thereby disrupting tissues with low elasticity, such as atheromas and thrombi. The ultrasound was delivered through catheters to prevent damage to normal tissues near the sites of the occlusions.

Kudo and co-workers are the first to report the use of noninvasive ultrasound to increase the efficacy of systemic t-PA. (Kudo S., Furuhata H., Hara M., Maie K., Hamano K., Okamura T. "Noninvasive Thrombolysis with Ultrasound"; *Circulation*, 80:supp II-345 (1989) (abstract); Kudo S. "Thrombolysis with Ultrasound Effect", *Tokyo Jikeikai Med J.*, 104:1005-1012 (1989); and Hamano K., Fujinaga T., Muto M., Yoshizawa S., Kudo S., Hara M., Okamura T., Furuhata H., "Thrombolysis by Transcutaneous Ultrasonic irradiation, *Circulation*, 82:III-309 (1990) (Abstract).) It was found that transcutaneous ultrasound that was delivered in a continuous mode at a frequency of 200 kHz could enhance t-PA-induced fibrinolysis in a canine model of femoral arterial thrombi. The instantly disclosed and claimed invention varies from the methods taught in those publications, since the inventive method uses intermittent (pulsed mode) ultrasound and/or a fluid interface between the skin of the patient and the transducer of the ultrasound generator.

Lower extremity deep venous thrombosis (DVT) incidence in the United States is greater than 250,000 cases annually. Pulmonary embolism is the primary cause of at least 50,000 deaths annually. The incidence of clinical DVT is 1 in 500 in general hospital patients. In unselected patients undergoing elective major general or orthopedic surgery without prophylaxis the incidence of DVT is reported to be 20% to 30%.

Heparin is often used to prevent thrombus propagation. Plasminogen activators (PA's) are used to lyse thrombi, but DVT are often resistent to both of these therapies. Complete thrombolysis is difficult to achieve. Plasminogen activators are particularly effective thrombolytic agents when incorporated into a forming thrombus. It is believed that limited surface binding and penetration into the thrombus by PA may explain difficulties in achieving complete thrombolysis.

Raising the dosage of t-PA administered beyond 100 mgm for lysis of acute thrombosis increases the number of hemorrhagic complications and, for this reason, dosing above this level is not desirable.

Most investigation of ultrasound bioeffects have been directed to safe exposure of human for diagnostic purposes. However, therapeutic applications to treat injuries to soft tissue and for ultrasonic aspiration have proven useful in neurosurgery and soft tissue resections. Reports of studies of ultrasound by Kudo on dogs do not discuss some of the problems related to temperature increases arising during exposure for therapeutic uses. No disclosure of use of ultrasound to prevent formation of thrombosis has previously been disclosed.

A model frequently used in assessing thrombosis has been the rabbit with jugular vein thrombosis. Previous studies with this model indicate that the rate and extent of thrombolysis are related and that complete lysis of thrombus is very difficult to achieve. Ultrasound that is used in physiotherapy is delivered at a frequency of 1 MHz, which can cause acoustic streaming, or wave-media interactions that promote agitation of solute and micro-particulate matter without inducing cavitation or tissue damage. This property of ultrasound suggests that it may have the potential for gentle perturbation of a clot, thereby exposing additional fibrin for binding to the plasminogen activator.

Ultrasound travels through fluid and soft tissue by wave propagation. The number of ultrasound waves per unit area is a measure of power which is usually expressed as watts/cm$^2$. As ultrasound travels through soft tissue it pushes fluids in the direction of the beam. Another effect is the momentary absorption of ultrasound energy by dissolved gases in fluid which results in expansion and then redissolution of the gas. These effects are referred to as acoustic microstreaming and cavitation. The end result of ultrasound interactions with soft tissue is attenuation of the beam and generation of heat. Attenuation increases as frequency increases, which results in a decreasing penetration into soft tissue with increasing ultrasound frequencies. The 1 MHz frequency used in these experiments will maintain 30% of original energy after traversing 10 cm of soft tissue. At power levels of 3.0 watts/cm$^2$ (average power), harmful effects of ultrasound have been noted only under conditions which generate enough heat to cause thermal injury.

Clinical experience with plasminogen activators have resulted in findings similar to those noted in rabbit studies. The greatest success has been attained in treatment of coronary artery thrombi, but challenges remain: 1) to decrease the mean time required for restoration of coronary artery flow following administration of the plasminogen activating agents and 2) in the setting of acute myocardial infarction or venous thrombosis, to increase the percent of patients receiving plasminogen activators who will have successful restoration of blood flow. Raising dosage of plasminogen activators increases the number of hemorrhagic complications and, for this reason, dosing at high levels is not a routine option to improve results of therapy.

SUMMARY OF THE INVENTION

It is the purpose of this invention to provide improved methods for prevention or treatment of thrombosis, including deep venous thrombosis (DVT) and acute arterial thrombosis such as coronary artery thrombosis, whilst avoiding damage to the surrounding tissue. The method of the invention comprises administration of plasminogen activators in conjunction with ultrasound in a manner that will provide improved protection of the surrounding tissue. The methods of the invention include administration of intermittent (pulse mode) ultrasound and the imposition of a fluid-containing barrier between the ultrasound source and the patient's skin.

It is also a purpose of this invention to provide a means for preventing formation of thrombi by administration of small doses of plasminogen activating agents along with intermittent ultrasound to patients who are likely to suffer from formation of thrombi. Particularly at risk are older patients that are immobilized or patients whose injuries have caused decreased circulation in the extremities.

DETAILED DESCRIPTION OF THE INVENTION

The invention described herein teaches means of effectively treating patients suffering from thrombosis, particularly deep venous thrombosis whilst avoiding injury to the surrounding tissue. The invention also provides means of preventing formation of thrombi using minimal dosages of plasminogen activators. The most commonly used plasminogen activators are strepokinase, urokinase, and t-PA. Additional agents that have been tested for use as plasminogen activators include analogues produced by known means including acylation of the plaminogen moiety or attaching to the molecule of the plasminogen activators targeting antibodies, including antifibrin antibodies. An example of such an analog is the p-anisoylated derivative of Lys-Plaminogen-Streptokinase activator complex. The plasminogen activators have been made by recombinant bioengineering methods. The term "plasminogen activating agents" or the particular compounds named herein are to be considered to include such analogues of the named compounds. The analogues may be administered by the inventive method taught herein. Because the amounts of plasminogen activating agents required to prevent formation of thrombi are much lower than amounts required to treat patients who have thrombosis, patients who are likely to suffer from formation of thrombi may be beneficially treated prophylactically. The use of intermittent ultrasound and of the fluid barrier between the ultrasound source and the skin avoid exposure of the tissues to excessive heat and injury during treatment.

Maximum routine dosage used for t-PA in humans is 100 mg. in 24 hrs. Often half the dosage is administered as an intravenous bolus and the remainder given over the next 4 to 12 hours. The plasma half-life of t-PA is less than 15 minutes, but its clinical effectiveness is often noted to lag beyond the time of expected peak plasma levels. Routine measurement of t-PA is not performed during therapy, but a local plasma activity of 300 IU/ml (as determined by calculation rather than clinical testing) could be maintained for 8–10 hours by continuous local infusion of the standard dose, with peak systemic plasma activities to 5000 IU/ml. probably occurring during the acute administration of a t-PA bolus.

It was found, in in vitro testing, that ultrasound as administered by the inventive method shortened the time for 50% clot lysis to as little as half the time required without the ultrasound and that absolute lysis was increased by 30% to 500% by use of intermittent ultrasound.

Figure 1:
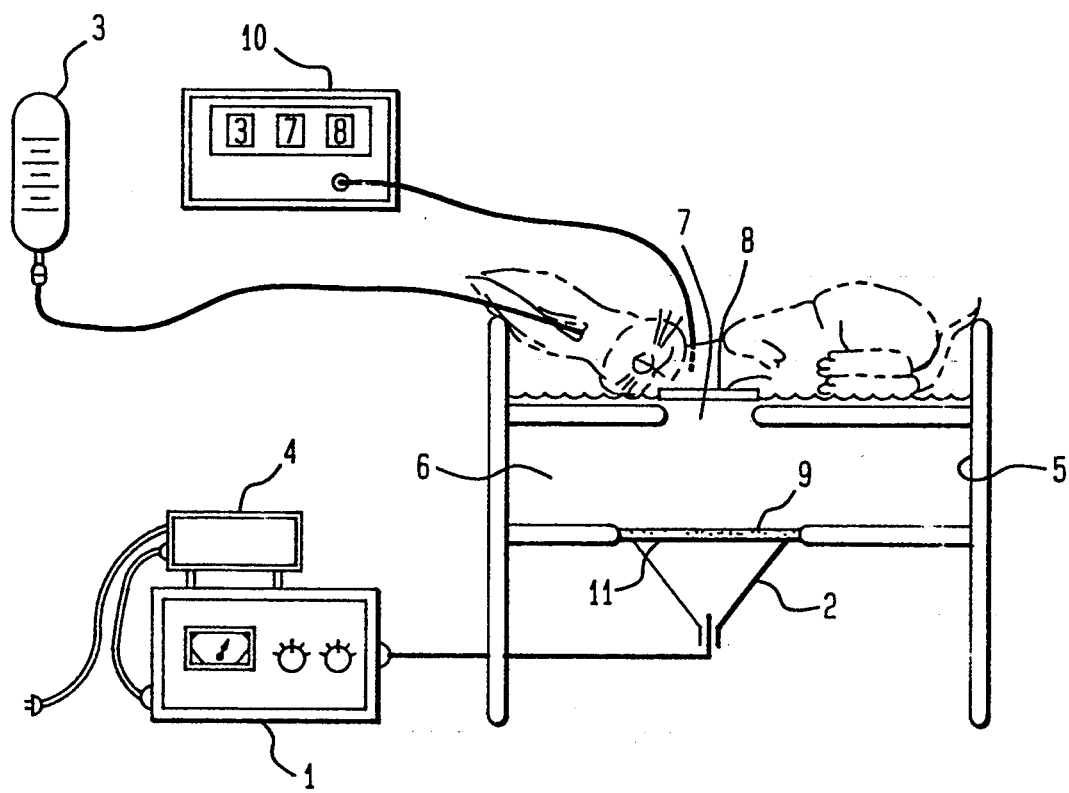
FIGS. 1 and 2 are a schematic representation of the equipment used in the rabbit experiments for the administration of t-PA, delivery of ultrasound, and monitoring of soft tissue temperature.

The imposition of a liquid-containing interface between the transducer of the ultrasound generator and the patient may be accomplished in any manner which allows the resonance to be transmitted to the skin. A bladder of fluid within an enclosure wherein the enclosure has openings positioned in such a manner that the membrane surrounding the liquid is exposed at two points: (1) at the area where the ultrasonic effects are to be delivered to the patient and (2) at the area wherein the ultrasonic generator surface would in contact with the liquid-filled bladder membrane. FIG. 1 shows an example of use of such an array wherein a ultrasound generator (1) with a timer (4) has a transducer (2) with a contact surface (11) that contacts a membrane (9) and (7) that encloses a liquid (6). The membrane is in an enclosure (5). The mammal is placed with the thrombus (8) against the membrane. The intravenous fluid for infusion (3) may contain the plasminogen activating agent. A temperature monitor may be used to assess thermal effect on the tissues near the thrombus. The liquid-containing interface may also be provided by using a bladder containing fluid without an enclosure around it. It is also possible to provide the fluid interface by using a gel on the body at the point of contact with the ultrasound generator transducer.

Figure 2:
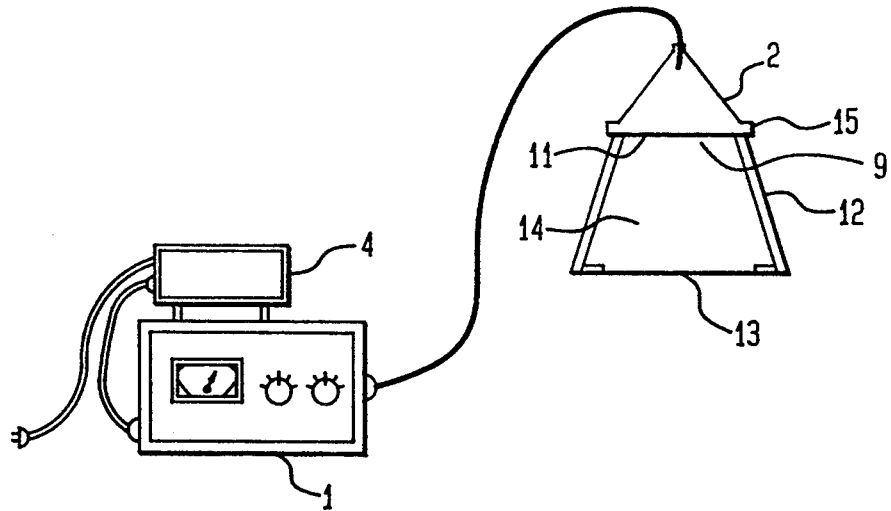

The bladder containing liquid can be made specifically to fit over the contact surface of the transducer of ultrasound generator. Such an arrangement is shown in FIG. 2 wherein the ultrasound transducer (2) has attached thereto a liquid containing bladder (14) in an enclosure (12) which is clipped into place with fastening means (15) and wherein one membrane of the bladder (9) is against the contact surface of the transducer (11) and is held in place by fastening means (15). Fastening means may be any means known in the art which will prevent a gap between the contact surface of the transducer and the membrane from the bladder containing liquid. For example, the enclosure may have a rim which will clip onto a complimentary ridge on the transducer. The preferred range of frequency for purposes of practicing this invention is 0.1–3MHz with a preferred power range of 0.5–3 watts/cm². The frequency of ultrasound determines the potential depth of penetration through fluid and soft tissue. Ultrasound travels very efficiently through water, with 95% of initial power conserved after traveling 10 cm. When traveling through soft tissue, only 30% of initial power is conserved after traveling 10 cm. Loss of ultrasound power or attenuation is the consequence of ultrasound interaction with the media. The end result of all interactions is the generation of heat. Using the methods of the invention, ultrasound treatment did not raise soft tissue temperatures in the region of ultrasound effect. In the rabbit model, serum CPK values were not altered with ultrasound treatment and histologic examination of the veins did not disclose change in the inflammatory response with ultrasound treatment.

The ability of noninvasive ultrasound, delivered at a frequency of within the range taught herein in an intermittent mode to enhance t-PA activity was evaluated in vitro and in vivo utilizing the rabbit jugular vein thrombosis model.

Materials and Methods

Materials:

Single chain human recombinant tissue plasminogen activator (t-PA, lot number N9102, specific activity 580,000 IU/mg) was purchased from Genentech, Inc., South San Francisco, Calif.; thrombin (2200 NIH U/mg) was from Sigma Chemical Company, St. Louis, Mo. Lysine Sepharose and Sephadex G-25 were from Pharmacia Fine Chemicals, Uppsala, Sweden; iodogen was from Pierce Chemical, Rockford Ill., and $^{125}I$ was purchased from Amersham Corp, Arlington Heights, Ill. Human serum albumin was from Miles Inc, Elkhart, Ind. Plasminogen was purified from human fresh frozen plasma by affinity chromatography on a lysine-Sepharose column. Plasminogen was in the glu form as assessed by SDS-gel electrophoresis and had a specific activity of 20 CTA U/mg.

Preparation of $^{125}I$-Fibrinogen:

Fibrinogen was purified from fresh human plasma by glycine precipitation and was radiolabeled with $^{125}I$ by the iodogen technique. Two ml of fibrinogen (1.8 mg/ml) in 0.05M Tris-HCl, 0.10M NaCl, 0.025M sodium citrate, pH 6.8 was mixed with 400 $\mu$Ci $^{125}I$ at 22° C. for 2 to 3 minutes in a scintillation vial pre-coated with 20 $\mu$g iodogen. Unbound $^{125}I$ was separated from labeled fibrinogen with a Sephadex G-25 column. The radiolabeled fibrinogen was 88% clottable and had a specific activity of $3.0 \times 10^7$ cpm/mg.

Ultrasound:

A 1MHz ultrasound generator (Amrex Synchrosonic U/50, Amrex-Zetron, Inc., Hawthorne, Calif.) was used to provide continuous mode, or intermittent mode ultrasound output. For intermittent ultrasound, the "on" interval was two seconds, followed by a rest interval of two seconds. Ultrasound was tested at two different intensities (expressed as spatial-average temporal-average intensities) of 0.375 watt/cm$^2$ and 1.75 watt/cm.$^2$ Ultrasound was delivered through water from a planar transducer (surface area, 23 cm$^2$), which was 6 cm from the thrombus for both in vitro and in vivo experiments. At this distance, ultrasound was delivered as a cylindrical beam. The attenuation was less than 1% in a 6-cm path in water. In tissue, the intensity was reduced by 11% in a 1-cm path.

In Vitro Thrombolysis:

Blood was obtained by venipuncture from one normal volunteer under a protocol approved by the Human Use Committee of the Walter Reed Army Institute of Research. Whole blood clots were prepared by adding thrombin (50 $\mu$l, 15 NIH U) to a mixture of 3 ml freshly obtained blood and 300 $\mu$l $^{125}I$-fibrinogen (0.7 $\mu$Ci) in a 10$\times$75 parafilm tube.

After incubation at 22° C. for two hours, the clots were added to two beakers that were in a water bath that was maintained at 37° C. The beakers each contained 100 ml supernatant. In one of the two beakers, the ultrasound transducer was placed into direct contact with the supernatant, and the clot was at the bottom of the conical beaker or 6 cm from the face of the transducer. The surface area of each beaker was 43 cm.$^2$ The walls of the pyrex beakers were 2 mm in thickness and the angle between each beaker and the external perpendicular support was 23.° Conical beakers were used so that thrombus would not drift out of the range of the ultrasound beam. The temperature of the supernatant was monitored throughout the experiment with a thermometer that was accurate to 0.1° C. Each paired experiment (at a given t-PA concentration and buffer composition) consisted of two clots, one of which was exposed to ultrasound. The supernatant was either 100 ml Tris-albumin buffer (0.15M NaCl, 0.02M Tris-HCl, pH 7.40 containing 1% human serum albumin) or 100 ml human plasma obtained as fresh frozen plasma. In the six paired experiments using fresh frozen plasma, six units of plasma, each from a different donor was used; plasma from a single unit was used for each paired experiment. After the addition of the clot to the supernatant, fibrinolysis was initiated by adding t-PA at final concentrations ranging from 3 to 3000 IU/ml.

Fibrinolysis was monitored by determining the radioactivity of the whole clot in a gamma counter (Searle Model 1185, Searle Diagnostics, Inc., Des Plains, Ill.) before addition to the supernatant. Immediately after the addition of the clot to the beaker and before the addition of the t-PA, a 200 $\mu$l aliquot of the supernatant was tested for radioactivity, followed by serial sampling throughout the 200 min experiment. Sampling intervals ranged from 10–15 min during the initial phase of the lysis to 30–40 min after the plateau was achieved. The residual radioactivity in the clot was determined at 200 min.

Percent lysis was calculated according to the following formula:

$$\frac{500 \text{ (Supernatant CPM time } X - \text{Supernatant CPM time 0)}}{\text{(Thrombus CPM time 0 } - \text{ background)}} \times 100.$$

In Vivo Thrombolysis:

The experimental protocol, which was approved by the Walter Reed Army Institute of Research Animal Committee, used male New Zealand White rabbits weighing between 3.0–3.5 kg.

Thrombosis Model:

The rabbit jugular vein thrombosis model was chosen because of its established value in the testing of t-PA for clinical use and the relative simplicity of the required surgical procedure and animal care. Anesthesia was induced with the intramuscular injection of 50 mg/kg Ketamine (Vetalar, Parke-Davis, Morris Plains, N.J.) and 0.1 mg/kg xylazine (Rompun, Miles Lab. Inc., Shawnee, Kans.). The animals were intubated and anesthesia was maintained with 1.5–2.5% halothane (Halocarbon Lab. Inc., Hackensack, N.J.) administered through a model 50122 Bickford vaporizer (A.M. Bickford Inc., Wales Center, N.Y.).

The jugular vein was isolated as previously described with ligation of all side branches except the facial vein. A venotomy in the facial vein then allowed a 0.038 O.D. inch polyethylene catheter (Intramedic tubing, Clay Adams, Parsippany, N.J.) to be introduced and a one ml aliquot of blood to be withdrawn. The blood was then mixed with 100 µl (1 µCi) $^{125}$I-fibrinogen (human) and kept on ice to prevent clotting. Next the jugular vein was atraumatically occluded proximal and distal to the facial vein with microvascular clamps (Scanlan Int., Inc., St. Paul, Minn.). A 4-0 silk thread soaked in human thrombin solution was placed in a small polyethylene catheter which was inserted into the venotomy in the facial vein and guided into the jugular vein. The radiolabeled blood (0.5 ml) was introduced into the jugular vein through the facial vein to create a thrombus around the 4-0 silk thread. The catheter in the facial vein was removed, the facial vein ligated around the thread, and the end of the thread was brought out to the skin through a small puncture to facilitate percutaneous removal at the completion of the experiment. The microvascular clamps were removed and the skin was closed.

A temperature probe (2400 series temp. probe, Electromedics Inc., Englewood, Colo.) to be used for temperature monitoring during the experiment was inserted into the neck through a separate skin puncture. The animal to receive ultrasound was positioned on a specially designed treatment table with an enclosed water bath maintained at 36.5°-38.5° C. (FIG. 1). The other animal was positioned in a similar fashion on a circulating water warming blanket also maintained at 36.5°-38.5° C.

Experimental Protocol:

To determine the effect of ultrasound on t-PA induced fibrinolysis, a series of paired experiments were performed in which both animals received t-PA and one of each pair received ultrasound in addition to the t-PA. Intermittent ultrasound (1 MHz, 1.75 watt/cm$^2$ with a two-second "on" interval and a two-second rest interval) was delivered throughout the experiment to the neck of the animal from a fixed transducer through a six cm depth water bath (FIG. 1). The distance was chosen so that the ultrasound beam could provide adequate coverage of the site of potential thrombosis in a human model. Controls for the rabbits receiving t-PA and ultrasound were four rabbits that received ultrasound and no t-PA.

In six paired experiments animals received t-PA at a dose of 1 mg delivered intravenously during the first 30 min of the experiment. An additional six pairs of animals received t-PA at a dose of 2 mg. In this group, 1 mg t-PA was administered during the first 30 minutes followed by 1 mg from 35 to 185 min. One control animal in this group died of post-operative respiratory insufficiency; therefore, only five paired studies are reported.

All animals received maintenance fluid and t-PA through a marginal ear vein cannula ipsilateral to the jugular vein thrombus. One mg t-PA was diluted in 5 ml of 0.3M NaCl, 0.01% Tween 80 (Aldrich Chemical Co., Arlington Heights, Ill.) and administered with a constant infusion pump (Sage Instruments, Cambridge, Mass.). Fibrinolysis was monitored by obtaining a 2-min count of radioactivity over the neck of each animal at time zero (before the infusion of t-PA) with a calibrated gamma ratemeter (model 2221 scaler ratemeter, Ludlum Measurements Inc., Sweetwater, Tex.). This was followed by serial counts throughout the experiment, with background counts obtained as well at each time point.

Percent lysis was calculated according to the following formula:

$$\frac{(\text{Cervical CPM time 0} - \text{Cervical CPM time } X)}{(\text{Cervical CPM time 0} - \text{background})} \times 100.$$

Plasma fibrinogen and serum plasminogen were measured with functional assays as described by Hassett, et al. (*Thromb Res* 43: 313–323 (1986)).

Toxicity Studies:

To determine the extent of tissue injury sustained due to insonation, the levels of creatinine phosphokinase (CPK, Encore Chemistry System, Baker Instruments Inc., Allentown, Pa.) were measured in serum at time 0, 200 min, 24 hours and seven days in the pairs of rabbits receiving 1 mg t-PA in the presence and absence of ultrasound.

A blinded histologic examination for pulmonary emboli was performed in four rabbits treated only with t-PA and in eight rabbits that received combination t-PA and ultrasound.

The effect of insonation on jugular veins in the absence of thrombosis was studied histologically in three pairs of animals. Each pair underwent a sham operation to include catheterization of the jugular vein. Then one animal in each pair received 200 minutes of intermittent ultrasound (1MHz, 1.75 watt/sec$^2$) directed at the jugular vein. Seven days later the animals were killed with a 5 ml intravenous injection of sodium pentobarbital (Euthanasia-6). The jugular vein segments and lungs were removed and immersion-fixed in neutral buffered 10% formalin. Tissue was subjected to blinded histologic evaluation for inflammatory changes in vein segments.

Statistical Methods:

Summary thrombolysis data are reported as mean values and corresponding standard errors of the mean (SEM). Analysis of variance (ANOVA) was used to determine the statistical significance of differences in clot lysis due to effects of : (1) ultrasound (alone or in combination with t-PA) (2) concentration of t-PA, and (3) time of measurement. This analysis included time as a repeated measures factor and took into account the paired nature of the experimental design for comparing clots receiving ultrasound and t-PA with those receiving t-PA alone. This feature results because each experimental run at a given t-PA concentration included two clots studied in parallel—one receiving ultrasound and t-PA, the other t-PA alone. The 50 minute and 200 minute time points (the repeated measures factor) were analyzed to determine early and late effects of insonation (reflecting rate and extent of fibrinolysis) for all in vitro studies. Similar analyses were used for the in vivo data at 50 and 100 minutes, a time when fibrinolysis had reached a plateau. The t-test (paired or unpaired as appropriate) was used when only two groups were compared. Observed significance levels (p-values), involving effects of ultrasound derived from t-tests or from 1 degree of freedom F tests (F (1, df), were two sided. A p value <0.05 was considered to be significant. Analyses based on transformed data (logs) yielded similar results. The ordinary (Pearson's) correlation coefficient was used as a measure of correlation between two variables.

Results:

Comparison of Different Ultrasound Modes on T-PA Induced Clot Lysis in Vitro

The optimal intensity of ultrasound for enhancement of clot lysis was determined by exposing blood clots in Tris-albumin buffer containing t-PA (300 IU/ml) to ultrasound at a frequency of 1 MHz and an intensity of 1.75 watt/cm$^2$ or 0.375 watt/cm$^2$ for 200 min. Intermittent or continuous ultrasound at an intensity of 0.375 watt/cm$^2$ did not enhance thrombolysis. Continuous ultrasound at an intensity of 1.75 watt/cm$^2$ increased the temperature of the medium from 37.0° C. to 39.0° C. within ten minutes of initiation and maximally by 5° C. during the course of the 200 min experiment. This mode was therefore not evaluated further. However, intermittent ultrasound at an intensity of 1.75 watt/cm$^2$ caused significant enhancement of lysis at 200 min ($64\pm10\%$ versus $42\pm5\%$, $p<0.05$) without increasing the temperature of the surrounding medium by more than 1° C. Therefore, intermittent ultrasound at an intensity of 1.75 watt/cm$^2$ and a frequency of 1MHz was chosen for all further studies.

Effect of Intermittent Ultrasound (1MHz, 1.75 watt/cm$^2$) on Clot Lysis Induced with Different Doses of T-PA Studies were conducted in the absence and presence of intermittent ultrasound and t-PA at four different concentrations (3, 30, 300 and 3000 IU/ml) to determine if ultrasound affected the rate and extent of t-PA induced fibrinolysis. Differences in mean clot lysis due to effects of ultrasound and t-PA concentration were determined using repeat measures ANOVA, with the 50 min time point reflecting the rate of fibrinolysis and the 200 min time point reflecting the extent of fibrinolysis. The overall differences in mean clot lysis among the four t-PA concentrations were significant ($F(3,10)=8.3; p<0.005$) with the extent of fibrinolysis increasing in a dose-related manner for thrombi receiving ultrasound or no ultrasound.

The overall difference in mean clot lysis between thrombi receiving ultrasound and no ultrasound was highly significant ($F(1,10)=52.2; p<0.001$) with differences in time course consistent across all four t-PA concentrations. There was also a significant difference in the two groups (ultrasound versus no ultrasound) with respect to the rate of lysis as measured at 50 min ($p<0.001$) and extent of clot lysis as measured at 200 min ($p<0.001$), when analyzed separately. At the lowest concentration of t-PA (3 IU/ml), ultrasound caused a 100% enhancement of lysis as determined at 200 min, and an approximate 50% increase at the higher t-PA concentrations.

Effect of Plasma and Plasminogen on Fibrinolysis Induced by t-PA and Ultrasound (1MHz, 1.75 watt/cm$^2$)

In paired experiments, clots were incubated with fresh frozen plasma to which t-PA had been added at a final concentration of 300 or 3000 IU/ml, and one clot in each pair was exposed to intermittent ultrasound. Ultrasound induced a significant increase in the extent of thrombolysis as determined with the repeat measures ANOVA utilizing 50 and 200 minute data at both tPA concentrations ($F(1,4)=36.9; p=0.004;$). In all six paired experiments (three pairs at 300 IU/ml and three pairs at t-PA 3000 IU/ml) the thrombus exposed to ultrasound and t-PA underwent greater lysis than the thrombus incubated with t-PA alone.

When clots were exposed to ultrasound and t-PA at a concentration of 300 IU/ml, the lysis at 200 min was $75\pm7\%$ compared to $50\pm2\%$ when clots were incubated with t-PA alone. Furthermore, ultrasound reduced the time to reach 50% lysis from 200 min to 96 min.

For the clots exposed to t-PA at a final concentration of 3000 IU/ml, the mean time to reach 50% lysis was reduced from 98 to 48 minutes in the presence of ultrasound. Clot lysis at 200 minutes was $91\pm11\%$ in the presence of insonation compared to $62\pm5\%$ in the absence of ultrasound.

Fresh frozen plasma derived from a single donor was used in each paired experiment. The mean plasminogen concentration in the plasmas (n=6) used for these experiments was $3.8\pm0.2$ CTA U/ml. In additional experiments, clots were incubated with t-PA (3000 IU/ml) in Tris-albumin buffer containing purified plasminogen at a concentration of 1.2 CTA U/ml. The same degree of lysis was achieved at the lower concentration of plasminogen (Table 1).

The results of thrombolysis experiments with 3000 IU/ml t-PA in Tris-albumin, plasma, and Tris-albumin containing plasminogen are summarized in Table 1. In the absence of ultrasound, there was no significant difference among the rates of lysis for clots that were exposed to t-PA that was in buffer, plasma or buffer containing plasminogen ($p>0.05$). There was also no difference in lysis rates for clots that were incubated with these different supernatants in the presence of ultrasound, although a trend toward further improved thrombolysis with plasma and plasminogen compared to buffer is evident at 200 minutes (Table 1).

Effect of Insonation on t-PA-induced Thrombolysis In Vivo:

Data obtained in in vivo studies using the rabbit jugular vein thrombosis model were conducted on paired groups of rabbits that received t-PA in the presence or absence of ultrasound, four rabbits received only ultrasound and no infusion of t-PA. In these "ultrasound only" controls, clot lysis was $9\pm5\%$ at 50 min. and $6\pm10\%$ at 100 min.

Lysis in the rabbits that received 1 mg t-PA and ultrasound was increased at 50 min. compared to that of rabbits receiving t-PA alone ($41\pm14\%$ versus $20\pm12\%$ $p=0.12$) The increase at 100 min., a time when lysis had reached a plateau, was sustained ($55\pm11\%$ versus $30\pm12\%$, $p=0.11$). Furthermore, four pairs out of six showed improved thrombolysis with ultrasound.

Clot lysis for the rabbits that received 2 mg t-PA and insonation compared to those that received only t-PA was $45\pm7\%$ versus $28\pm11\%$ ($p=0.10$) at 50 min and $50\pm12\%$ versus $40\pm12\%$ ($p=0.29$) at 100 min. Three pairs out of the five showed improved thrombolysis with ultrasound.

Although the overall difference (repeat measures ANOVA using data at 50 and 100 minutes for both t-PA doses) in mean thrombolysis between rabbits receiving insonation and t-PA and those receiving t-PA alone was not significant ($F(1,9)=2.7$; $p=0.13$;), differences favored insonation at both 50 and 100 minutes for both doses of t-PA. The contrast between insonation and t-PA versus t-PA alone was greatest at 50 minutes ($F(1,9)=).13$;), $p=0.09$) when the combined data for the two doses were analyzed. The extent of thrombolysis in the group receiving t-PA at a dose of 2 mg was not different from that receiving 1 mg ($p=0.73$).

In the rabbits receiving 2 mg t-PA alone there was no significant change in the levels of plasminogen and fibrinogen between the beginning and the end of the experiment at 200 min. Fibrinogen levels were $2.2\pm0.2$ mg/ml initially and then 1.6±0.3 mg/ml (p=0.13) at 200 min. Plasminogen levels were 3.9±0.3 CTA U/ml and then 3.7±0.2 CTA U/ml (p=0.6). In the rabbits receiving intermittent ultrasound and t-PA, there were significant changes in the levels of fibrinogen and plasminogen. The fibrinogen level decreased from 2.0±0.1 mg/ml at the beginning of the experiment to 1.1±0.3 mg/ml at 200 min (p=0.03). The plasminogen level decreased from 3.6±0.4 to 2.6±0.3 CTA U/ml (p=0.03). There was no significant change in the levels of fibrinogen of plasminogen in the four animals receiving intermittent ultrasound without t-PA. In this group, fibrinogen levels at the beginning and end of the experiment were 1.9±0.1 and 2.0±0.1 mg/ml (p=0.42), respectively, and the plasminogen levels were 4.2±0.3 and 4.0±0.2 CTA U/ml (p=0.33).

Investigation of potential insonation-induced injury.

No increases in temperature were observed for animals receiving intermittent ultrasound and t-PA compared to those receiving only t-PA. There was no difference in the CPK values between rabbits receiving intermittent ultrasound and 1 mg t-PA and those receiving 1 mg t-PA alone. Pulmonary emboli were not detected histologically in twenty sections from the lungs of four rabbits treated only with t-PA. Two out of the forty histologic sections from eight rabbits that received combination t-PA and ultrasound had a single embolus and each was located in a 1 mm arteriole.

Intermittent ultrasound did not induce endothelial changes in the rabbits that underwent a sham operation with catheterization of the jugular vein, and there was no evidence for thrombosis.

TABLE 1

Effect of Intermittent Ultrasound (US, 1 MHz, 1.75 watt/cm$^2$) on Clot Lysis Induced by t-PA (3000 IU/ml) in Buffer, Plasma, and Buffer Containing Purified Plasminogen

| t-PA (3000 IU/ml) | % Lysis at 50 minutes | | | % Lysis at 200 minutes | | |
|---|---|---|---|---|---|---|
| | US | No US | p* | US | No US | p |
| Buffer | 45 ± 12** | 33 ± 7 | 0.07 | 73 ± 12 | 62 ± 15 | 0.03 |
| Plasma | 50 ± 9 | 33 ± 4 | 0.05 | 91 ± 11 | 62 ± 5 | 0.03 |
| Plasminogen | 54 ± 5 | 35 ± 2 | 0.02 | 106 ± 6 | 77 ± 4 | 0.01 |
| Controls | US (No t-PA) | No US | p | US | No US | p |
| Buffer | 4 ± 1 | 1 ± 1 | 0.04 | 8 ± 1 | 3 ± 1 | 0.02 |

*P-values are those for the given time points at the single dose of t-PA. The differences in mean clot lysis incubated in buffer, plasma, or buffer with plasminogen are not significant (p > 0.05). Three paired experiments (ultrasound vs no ultrasound) were performed with each different incubation medium.
**Values are expressed as the mean ± SEM.

TABLE 2

Clot Lysis in Rabbits Receiving t-PA Alone or T-PA and Intermittent Ultrasound (US, 1 MHz, 1.75 watt/cm$^2$)

| | % Lysis at 50 min | | | % Lysis at 100 min | | |
|---|---|---|---|---|---|---|
| | US | NO US | p* | US | NO US | p |
| t-PA (1 mg) (n = 6 pairs) | 41 ± 14** | 20 ± 12 | 0.12 | 55 ± 11 | 30 ± 12 | 0.11 |
| t-PA (2 mg) (n = 5 pairs) | 45 ± 7 | 28 ± 11 | 0.10 | 50 ± 12 | 40 ± 12 | 0.29 |
| Controls: t-PA (0 mg) | 9 ± 5 | ND+ | | 6 ± 10 | ND | |

**Values are expressed as the mean ± SEM.
+ND is "not done."

While the practitioner will adapt dosage of medications given and time and frequency of exposure to intermittent ultrasound to meet the particular needs of the patients, dosing with the usually prescribed doses of the particular plasminogen activating agents will be appropriate. For adult humans, the dosage which is usually given for lysis of thrombi in the absence of use of ultrasound augmentation is appropriate. (See Table III.) However, because of the improved lysis resulting from use of the ultrasound, the lysis occurs more quickly. Therefore, the length of time that such dosages are used will be greatly decreased.

TABLE III

| | Streptokinase | Urokinase | t-PA* |
|---|---|---|---|
| Systemic use: | | | |
| Loading dose | 250,000 U (30 min) | 4,000 U/Kg (30 min) | 8 mg 1–3 min 50–60 mg/57 min. |
| | 100,000 U/Hr 12–72 hr. | 4,000 U Kg/Hr. 12–72 hr. | 20 mg/60 min. 20 mg/60 min. |
| Low dosage: | 5000–7500 U/hr | 15000–21000 U/Hr | 1–15 mg/hr |
| Duration | 24–72 hr. | 12–72 hr. | 3 hr. for high dosage |
| Local* use: | 10,000 U/hr | 400–5000 U/hr. | |

TABLE III-continued

| | Streptokinase | Urokinase | t-PA* |
|---|---|---|---|
| Duration | 12–72 hrs. | | |

*Total dosage of this agent should not exceed 100 mg for one course of treatment.
*"Local" indicates that the active agent was administered into the thrombus or near the thrombus in the blood vessel.
The lower dosages should be tried when the pulsed mode ultrasound is used. For prophylactic use, even lower dosages (up to 10 fold lower) are appropriate.

We claim:

1. A non-invasive method of lysing thrombi comprising the steps of:
   1) adminstering a plasminogen activating effective amount of at least one plasminogen activating factor to a patient suffering from thrombosis;
   2) placing aganist a body surface of said patient which is near said thrombus a liquid-containing structure or a material to form an interface aganist which the contact surface of the transducer of an ultrasound generator is placed; and
   3) adminstering intermittent (pluse mode) ultrasound at a thrombus lysing effective frequency and power such that said frequency and power are acoustic streaming-inducing and non-cavitational.

2. A method of claim 1 wherein the plasminogen activating agent is a t-PA.

3. A method of claim 1 wherein the plasminogen activating agent is a streptokinase.

4. A method of claim 1 wherein the plasminogen activating agent is a urokinase.

5. A method of claim 1 wherein the frequency is 0.1 to 3MHz and the power range is 0.5–3 watts/cm$^2$.

6. A non-invasive method of preventing formation of thrombi comprising the steps of:
   1) administering a plasminogen activating effective amount of at least one plasminogen activating factor to a mammal;
   2) placing aganist a body surface of said mammal which is near an area likely to develop a thrombus a liquid-containing structure or a material to form an interface aganist which the contact surface of an ultrasound generator transducer is placed; and
   3) administering intermittent (pulse mode) ultrasound at a thrombus lysing effective frequency and power such that said frequency and power are acoustic streaming-inducing and non-cavitational.

7. A method of claim 6 wherein the plasminogen activating agent is a t-PA.

8. A method of claim 6 wherein the plasminogen activating agent is a streptokinase.

9. A method of claim 6 wherein the plasminogen activating agent is a urokinase.

10. A method of claim 6 wherein the frequency is 0.1 to 3MHz and the power range is 0.5–3 watts/cm$^2$.

11. A non-invasive method of lysing thrombi comprising the steps of:
    1) administering a plasminogen activating effective amount of at least one plasminogen activating factor to a patient suffering from thrombosis;
    2) placing aganist a body surface of said patient which is near said thrombus a contact surface of an ultrasound generator transducer and
    3) administering intermittent (pulse mode) ultrasound at a thrombus lysing effective frequency and power such that said frequency and power are acoustic streaming-inducing and non-cavitational.

12. A method of claim 11 wherein the plasminogen activating agent is a t-PA.

13. A method of claim 11 wherein the plasminogen activating agent is a streptokinase.

14. A method of claim 11 wherein the plasminogen activating agent is a urokinase.

15. A method of claim 11 wherein the frequency is 0.1 to 3MHz and the power range is 0.5–3 watts/cm$^2$.

16. A non-invasive method of preventing formation of thrombi comprising the steps of:
    1) administering a plasminogen activating effective amount of at least one plasminogen activating factor to a mammal;
    2) placing aganist surface of mammal which is near said the area likely to develop a thrombus a contact surface of an ultrasound generator transducer; and
    3) administering intermittent (pulse mode) ultrasound at a thrombus lysing effective frequency and power such that said frequency and power are acoustic streaming-inducing and non-cavitational.

17. A method of claim 16 wherein the plasminogen activating agent is a t-PA.

18. A method of claim 16 wherein the plasminogen activating agent is a streptokinase.

19. A method of claim 16 wherein the plasminogen activating agent is a urokinase.

20. A method of claim 16 wherein the frequency is 0.1 to 3MHz and the power range is 0.5–3 watts/cm$^2$.

* * * * *